(12) United States Patent
Defretin et al.

(10) Patent No.: US 9,382,562 B2
(45) Date of Patent: Jul. 5, 2016

(54) **STRAINS OF *SERRATIA PLYMUTHICA* PRODUCING TURANOSE AND USES THEREOF**

(71) Applicant: ROQUETTE FRERES, Lestrem (FR)

(72) Inventors: Sophie Defretin, Bethune (FR); Damien Raeckelboom, Lestrem (FR)

(73) Assignee: ROQUETTE FRERES, Lestrem (FR)

( * ) Notice: Subject to any disclaimer, the term of this patent is extended or adjusted under 35 U.S.C. 154(b) by 2 days.

(21) Appl. No.: 14/401,603

(22) PCT Filed: May 15, 2013

(86) PCT No.: PCT/FR2013/051054
§ 371 (c)(1),
(2) Date: Nov. 17, 2014

(87) PCT Pub. No.: WO2013/171424
PCT Pub. Date: Nov. 21, 2013

(65) Prior Publication Data
US 2015/0126472 A1     May 7, 2015

(30) Foreign Application Priority Data
May 16, 2012    (FR) ...................................... 12 54484

(51) Int. Cl.
| | |
|---|---|
| *C12P 19/12* | (2006.01) |
| *C12R 1/425* | (2006.01) |
| *C12N 1/20* | (2006.01) |
| *A23L 1/30* | (2006.01) |
| *A23L 1/09* | (2006.01) |

(52) U.S. Cl.
CPC . *C12P 19/12* (2013.01); *A23L 1/09* (2013.01); *A23L 1/30* (2013.01); *C12N 1/20* (2013.01); *C12R 1/425* (2013.01); *A23V 2002/00* (2013.01)

(58) Field of Classification Search
CPC ........... A23V 2002/00; A23V 2250/62; A23V 2200/10; A23V 2250/206; A23V 2250/636; A23V 2250/628; A23V 2250/606; C12R 1/425; C12R 1/01; C12R 1/07; C12R 1/39; C12N 15/8245; C12N 1/20; C12N 15/8246; C12N 9/90; C12P 19/12; C12P 19/18; A23L 1/09; A23L 1/30; A23L 1/2363
See application file for complete search history.

(56) References Cited

U.S. PATENT DOCUMENTS

2009/0221525 A1     9/2009   Coy et al.

FOREIGN PATENT DOCUMENTS

WO    WO 2007/107295      9/2007

OTHER PUBLICATIONS

Database WPI, Thomson Scientific, Accession No. 2010-C73136, Mar. 2, 2010, pp. 1-3, XP-002691248.
Wang, R. et al. "Development of an efficient bioprocess for turanose production by sucrose isomerisation reaction of amylosucrase" *Food Chemistry*, 2012, pp. 773-779, vol. 132, No. 2.

*Primary Examiner* — Debbie K Ware
(74) *Attorney, Agent, or Firm* — Saliwanchik, Lloyd & Eisenschenk

(57) ABSTRACT

The present invention relates to a strain of *Serratia plymuthica* capable of producing turanose and mutants of said strain. Methods of producing turanose utilizing the disclosed strains of *Serraitia plymuthica* are also provided.

19 Claims, No Drawings

STRAINS OF *SERRATIA PLYMUTHICA* PRODUCING TURANOSE AND USES THEREOF

CROSS-REFERENCE TO RELATED APPLICATION

This application is the U.S. national stage application of International Patent Application No. PCT/FR2013/051054, filed May 15, 2013.

FIELD OF THE INVENTION

The present invention relates to a strain producing turanose and to the uses thereof.

TECHNOLOGICAL BACKGROUND OF THE INVENTION

Turanose is an isomer of sucrose comprising a glucose unit and a fructose unit linked via an $\alpha(1\rightarrow3)$ bond. It is a typical sugar of honey, in which it is present in a low amount, generally between 0 and 3%.

It can, for example, be produced by partial hydrolysis of melezitose, thus producing an equimolar mixture of glucose and turanose (CS240545). In addition, it can also be produced through the action of a cyclomaltodextrin glucanotransferase of *Bacillus stearothermophilus* on a mixture of starch and fructose (JP5252974/93; Shibuya et al., 2004, J. Appl. Glycosci., 51, 223-227). The yield is only 45% and the method comprises two enzymatic steps.

Finally, it has been proposed to use a recombinant amylosucrase derived from *Neisseria polysaccharea* (NpAS) to convert sucrose to turanose (Wang et al., 2012, *Food Chemistry*, 132, 773-779). The yield is 56% and the method requires a recombinant enzyme.

It is known to those skilled in the art that turanose:
has a relatively weak sweetening power of 0.5 (the value 1 being assigned to sucrose) and a low cariogenicity,
can be readily crystallized, and
is highly soluble.

In addition, turanose is an inhibitor of $\alpha$-glucosidase, useful in the diagnosis of Pomp's disease.

It is also of interest in the food, cosmetic, pharmaceutical and diagnostic fields.

Turanose is also a message molecule. With other monosaccharides, turanose has thus been used to mimic the various sucrose signaling pathways in photosynthesis.

Turanose may also be involved in plant defense mechanisms, with the production of defensive substances via activation of MAPKs (Mitogen-Activated Protein Kinases).

Thus, alternative methods for producing turanose are useful and desired, in particular methods which are competitive at the industrial level.

SUMMARY OF THE INVENTION

Anxious to develop a production process which is much more efficient and much less expensive than those described in the prior art, the applicant company has, during its research, identified a novel strain which has the capacity to produce turanose.

The present invention therefore relates to a *Serratia plymuthica* bacterial strain capable of producing turanose. This strain was deposited on Mar. 7, 2012, with the CNCM [National Collection of Microorganism Cultures] under number I-4604.

It also relates to a *Serratia plymuthica* strain characterized in that it is capable of producing turanose, and in that it is obtained from the I-4604 strain by culturing, mutagenesis or genetic modification of said strain.

Preferably, the *Serratia plymuthica* strain according to the present invention is capable of producing turanose with a turanose/sucrose weight yield of at least 20%, 30%, 40% or 50%.

The present invention relates to a method for producing turanose, comprising culturing the strain according to the present invention and recovering the turanose, and optionally purifying the turanose.

Preferably, the strain is cultured at a pH of between 5.5 and 7, an aeration of from 0.5 to 1.5 vvm, under agitation conditions of between 250 and 700 rpm, and at a temperature of from 25 to 38° C. In a manner which is in addition preferred, the strain is cultured at a pH maintained at 6, a temperature of from 27 to 30° C., agitation conditions of between 250 and 350 rpm, and an aeration of 1 vvm.

Preferably, the starting sucrose concentration in the production medium is between 100 and 300 g/l, preferably 200 g/l.

In one particular embodiment, the production medium comprises 2 to 6 g/l of yeast extract or 10 to 30 g/l of corn steep liquor (such as the SOLULYS 048E sold by the applicant company), preferably approximately 4 g/l of yeast extract. Preferably, the purification of the turanose comprises a fermentation must centrifugation step, steps of treatment with powdered black carbon and of filtration of the supernatant, a demineralization step, a step of ultrafiltration with a cut-off threshold at 1 kD, and then a filtrate crystallization step.

The present invention also relates to a turanose-rich composition capable of being obtained or obtained by means of the process according to the present invention. Preferably, it comprises at least 80% of turanose by total weight of DP2, 0.01% to 10% of trehalulose by total weight of DP2 and 0.01% to 5% of isomaltulose by total weight of DP2.

The present invention relates to a method for preparing a food composition, comprising the provision of turanose obtained by means of the method according to the present invention and the incorporation of the turanose obtained into the food composition. It also relates to a method for preparing a food composition, comprising the provision of a turanose-rich composition obtained by means of the method according to the present invention and the incorporation of the composition obtained into the food composition.

Finally, the present invention relates to a method for preparing a turanose-rich composition capable of being obtained or obtained by means of the process according to the present invention, intended for the food, cosmetic, pharmaceutical, diagnostic and phytosanitary fields.

DETAILED DESCRIPTION OF THE INVENTION

Entirely surprisingly, the applicant has succeeded in identifying and isolating a strain capable of efficiently producing turanose among a very large number of microorganisms derived from a soil sampling campaign.

The strain identified is a *Serratia plymuthica* bacterium and is herein called I-4604. It was filed on Mar. 7, 2012, with the CNCM under number I-4604. This strain may subsequently be denoted "I-4604" in the present application.

This strain has the advantageous property of producing turanose in large amounts. Indeed, it makes it possible to obtain turanose with a turanose/sucrose weight yield of more than 35%. More specifically, an average turanose/sucrose yield of approximately 38% has been observed when a molasses base has been used. This yield increases to more than 50% when a sucrose base is used.

This strain is absolutely original with regard to its capacity for producing turanose. Indeed, the inventors have also tested three strains of the same genus, namely *Serratia plymuthica* ATCC 15928, *Serratia ficaria* GRIMONT 4024, and *Serratia ficaria* DSM 4569. None of the strains tested by way of comparison has shown the slightest capacity thr producing turanose.

Thus, the present invention relates to the I-4604 strain and to a bacterium derived from this strain, for example by culturing, genetic engineering or mutagenesis thereof, which retains the property of producing turanose. The mutagenesis can be side-directed and/or random. In particular, the *Serratia plymuthica* strains according to the present invention have the capacity to produce turanose with a turanose/sucrose weight yield of at least 20%, 30%, 40% or 50%. Preferably, the yield is at least 30%.

The present invention relates to a composition comprising a *Serratia plymuthica* strain according to the present invention, in particular the I-4604 strain, and optionally a culture medium. Preferably, the culture medium is suitable for the production of turanose by the *Serratia plymuthica* strain according to the present invention, in particular the I-4604 strain. In particular, this medium comprises sucrose. Ideally, it comprises approximately 100 to 300 g/l, approximately 100 to 200 g/l or approximately 200 g/l of sucrose. More specifically, the culture medium can comprise sucrose and also yeast extract and/or corn steep liquor (such as the SOLULYS 048E sold by the applicant company).

It is understood in the present document that the term "approximately" means plus or minus 10%, preferably plus or minus 5%. For example, for a value of 100, "approximately 100" means between 90 and 110, preferably between 95 and 105.

The present invention relates to the use of a *Serratia plymuthica* strain according to the present invention, in particular the I-4604 strain, in a fermentation reaction. In particular, the present invention relates to the use of a *Serratia plymuthica* strain according to the present invention, in particular the I-4604 strain, for the production of turanose.

It also relates to a method for producing turanose, comprising culturing the strain according to the present invention and recovering the turanose, and optionally purifying the turanose. In particular, the culturing of the strain is carried out in the presence of sucrose under fermentation conditions suitable for the production of turanose.

Preferably, the strain has been subjected, before the production or fermentation step, to preculturing and subculturing steps. The preculturing and subculturing media comprise sucrose, for example from approximately 50 to 150 g/l of sucrose, preferably approximately 100 g/l. These media also comprise nutrients. In particular, they can comprise yeast extracts and/or corn steep liquors (such as the SOLULYS 048E sold by the applicant company).

For example, they can comprise 5-15 g/l of yeast extract and/or 5 to 30 g/l of SOLULYS 048E. In particular, they can comprise either approximately 10-15 g/l of yeast extract, or approximately 10-15 g/l of yeast extract and approximately 5 g/l of SOLULYS 048E, or approximately 30 g/l of SOLULYS 048E. In one preferred embodiment, they comprise approximately 10-15 g/l of yeast extract. The preculturing and subculturing steps are carried out at a temperature of from 25 to 38° C., preferably from 27 to 30° C., and in particular at approximately 30° C. The preculturing step can last from 10 to 30 h, preferably approximately 15 to 25 h. The subculturing step can last from 5 to 25 h, preferably approximately 10 to 20 h. The starting pH can be between approximately 5.5 and approximately 7. In one preferred embodiment, the starting pH is approximately 7. The agitation can be between approximately 100 and 200 rpm (revolutions per minute). It is preferably approximately between 150 and 170 rpm.

Preferably, the sucrose is present in the production medium at an initial concentration of between approximately 100 and approximately 300 g/l. Preferably, it is present at an initial concentration of approximately 100 to 200 g/l. In one preferred embodiment, it is present at an initial concentration of approximately 200 g/l. The sucrose can be added in purified form or in the form of molasses. It can be added to the culture medium at the beginning of production or fermentation, several times during production or fermentation, or continuously during production or fermentation. In one preferred embodiment, it is added to the culture medium at the beginning of production or fermentation.

Regarding the pH conditions, it has been determined, during the optimization of the turanose production, that the pH can be between approximately 5.5 and 7, preferably between approximately 5.5 and approximately 6.5, even more preferably at approximately 6. Preferably, the pH is maintained during the production step. In one embodiment, the pH is maintained at approximately pH 6 during the production step.

Regarding the agitation conditions, the culturing is carried out with agitation, in particular with agitation between approximately 250 and approximately 700 rpm, preferably between 300 and 500 rpm. The agitation can be carried out using a magnetic bar or any other means known to those skilled in the art. In one embodiment, the culturing is carried out with agitation at approximately 300 rpm.

Regarding the aeration conditions, the culturing is carried out with an aeration of from 0.5 to 1.5 vvm (volume of air per minute and per volume). In one embodiment, the culturing is carried out with an aeration of approximately 1 vvm.

Regarding the temperature conditions, the culturing is carried out at a temperature of between approximately 25 and approximately 38° C. In one embodiment, the culturing is carried out at a temperature of between 27 and 30° C.

In one particular embodiment, the production medium comprises 2 to 6 g/l of yeast extract or 10 to 30 g/l of SOLULYS 048E, preferably approximately 4 g/l of yeast extract.

The culturing period can be determined by a maximum period conditioned by the total consumption of the sucrose. Preferably, the production culturing lasts at least 20 h, typically more than 30 h. IN one preferred embodiment, the production culturing lasts between 30 and 50 h, preferably approximately 40 h.

Preferably, the production step is carried out while observing one or more fermentation conditions as described in detail above. Preferably, all the conditions are observed.

After the fermentation step, the biomass can be recovered from the fermentation medium by any method known per se to those skilled in the art; for example, the biomass can be extracted from the fermentor and simply concentrated by microfiltration or centrifugation, or washed via a succession of concentrations-dilutions with an aqueous solution.

After the turanose harvesting step, the method can comprise a turanose purification step. This purification step can comprise a fermentation must centrifugation step, the supernatant being recovered. This supernatant can be the subject of additional purification steps. These purification steps can be chosen from carbon black treatment steps, filtration steps, ultrafiltration steps, demineralization steps, crystallization steps and combinations thereof. In one particular embodiment, the purification comprises a carbon black treatment step, a filtration step, a demineralization step, a step of ultrafiltration with a cut-off threshold of 1 kD and a crystallization step. In one preferred embodiment, it comprises these steps in the order in which they appear in the list.

The present invention also relates to a turanose of fermentative origin, capable of being obtained or obtained by fermentation of the *Serratia plymuthica* strain according to the present invention, in particular the I-4604 strain. Thus, it relates to the turanose capable of being obtained or obtained by means of the production method according to the present invention.

The present invention also relates to a composition rich in turanose capable of being obtained or obtained by fermentation of the *Serratia plymuthica* strain according to the present invention, in particular the I-4604 strain, or in other words by means of the production method according to the present invention. This composition comprises at least 80% of turanose by a total weight of DP2, preferably at least 85%, 90% or 95%. The term "DP2" is intended to mean "disaccharides". The composition can also comprise trehalulose and/or isomaltulose. The trehalulose is preferably present in the composition in proportions of between 0.01% and 10% by total weight of DP2. The isomaltulose is preferably present in the composition in proportions of between 0.01% and 5% by total weight of DP2. Preferably, the composition comprises trehalulose and isomaltulose. Other impurities may also be present, such as glucosylated glyceric acid, fructose, 2-ketoglutaric acid, citric acid, succinic acid and/or glucosylated lactic acid.

Turanose is particularly useful in the food industry. In particular, it can be incorporated into drinks, confectionery products, cereal bars, chocolate-flavored products, etc. Thus, the present invention relates to a food composition comprising a composition rich in turanose capable of being obtained or obtained by fermentation of the *Serratia plymuthica* strain according to the present invention, in particular the I-4604 strain.

Finally, the present invention relates to a method for preparing a food composition, comprising the provision of turanose obtained by means of the method according to the present invention and the incorporation of the turanose obtained into the food composition. Preferably, the food composition is a drink, a confectionery product, a cereal bar or a chocolate-flavored product.

It is also possible to take advantage of this composition in the food, cosmetic, pharmaceutical, diagnostic and phytosanitary fields.

The invention will be understood more clearly by means of the examples which follow, which are meant to be illustrative and nonlimiting.

EXAMPLES

Example 1

Production of Turanose from Sucrose by the I-4604 Strain and Comparison with Strains of the Same Genus and Species The fermentation of turanose from sucrose was tested with the I-4604 strain identified in the present invention and with other strains of the same genus and species, in particular the following strains:
*Serratia plymuthica* ATCC 15928
*Serratia ficaria* GRIMONT 4024
*Serratia ficaria* DSM 4569
1—Results
1.1—Fermentations Carried Out with the I-4604 Strain

|  | $[Sucrose]_c$ $g \cdot l^{-1}$ | $[Turanose]_p$ $g \cdot l^{-1}$ | $[Isomaltulose]_p$ $g \cdot l^{-1}$ | $Y_{Tur/Suc}$ % | Productivity $g \cdot l^{-1} \cdot h^{-1}$ |
|---|---|---|---|---|---|
| Molasses base | 120.2 | 53.1 | ND | 37.69 | 1.36 |
|  | 123 | 54.9 | ND | 38.19 | 1.41 |
| Sucrose base | 187.4 | 103.4 | ND | 46.37 | 2.66 |
|  | 185.4 | 98.5 | ND | 44.91 | 2.53 |
|  | 134.7 | 68.5 | 8 | 50.12 | 1.77 |
|  | 194.2 | 94.8 | 4.2 | 48.16 | 2.45 |
|  | 194.6 | 99.6 | 5.1 | 50.11 | 2.55 |
| Sucrose base pH not regulated at beginning of fermentation | 182.5 | 103.8 | 5 | 52.44 | 2.66 |

$_c$ = consumed;
$_p$ = produced

The average weight yield based on the two beet molasses base fermentations is 37.9±0.2%. Its productivity is 1.4±0.05 g/l/h.

The performance levels obtained on the basis of the best three sucrose base fermentations (in bold in table 1) are the following:
weight yield: 48.2±1.5%
turanose titer: 99.3±3.5 g/l (for a base at 200 g/l of sucrose)
productivity: 2.55 ±0.1 g/l/h.

All the sucrose was consumed in 39 h of fermentation. It was noted during the analyses that the I-4604 strain does not produce gluconic acid.

It would appear that the weight yields are greater when the I-4604 strain is cultured under conditions where the pH is not regulated at the start (the pH falls to 5 after 14 h of fermentation).

1.2—Fermentations Carried Out with the ATCC 15928 Reference Strain

|  | $[Sucrose]_c$ $g \cdot l^1$ | $[Turanose]_p$ $g \cdot l^1$ | $[Isomaltulose]_p$ $g \cdot l^1$ | $Y_{Isom/Suc}$ % | Productivity $g \cdot l^1 \cdot h^{-1}$ |
|---|---|---|---|---|---|
| Sucrose base | 117.1 | 0 | 95 | 76.58 | 2.46 |
|  | 209.8 | 0 | 138.7 | 63.46 | 3.59 |
|  | 186.4 | 0 | 126.4 | 69.81 | 3.24 |

$_c$ = consumed;
$_p$ = produced

Under the same conditions as I-4604, this strain does not produce any turanose at all. On the other hand, as indicated in the literature, it produces isomaltulose and a little trehalulose (Kawaguti el al., *Food Chemistry*, 2010, Vol. 120, No. 3).

1.3—Fermentations Carried Out with the Other *Serratia ficaria* Strains Tested, GRIMONT 4024 and DSM 4569

They showed a growth similar to *S. plymuthica*, but produced neither turanose nor isomaltulose.

2—Conclusions

The strains were tested in triplicate under the same fermentation conditions. The results obtained are the following:

| Turanose/sucrose weight yield | Roquette I-4604 | 46.37% | 48.16% | 50.11% |
|---|---|---|---|---|
| | ATCC15928 | 0% | 0% | 0% |
| | Grimont 4024 | 0% | 0% | 0% |
| | DSM 4569 | 0% | 0% | 0% |

The I-4604 strain was compared to several *Serratia* strains, all tested under the same production conditions on sucrose substrate. Only the I-4604 strain produces turanose.

3—Materials and Methods

Procedure

The sample preparation comprised three steps: a reviving step, a preculturing step and a subculturing step. The reviving comprised three successive subculturings of the strain on agar medium. The preculturing was carried out for 16 h at 160 rpm and 30° C. in the preculture medium. The subculturing was carried out for 9 h at 160 rpm and 30° C. in the subculture medium.

Next, a fermentation step was carried out in DASGIP bioreactors with a starting volume of 1.500 ml. The fermentation lasted 39 h at 300 rpm, at 1 vvm (volume of air per minute and per volume) (90 l/h) while maintaining the pH at 6 with 5N sodium hydroxide.

Composition of the Media

Agar Medium

Sucrose: . . . 40 g/l

SOLULYS 048E: . . . 20 g/l

Peptone (Becton Dickinson): . . . 10 g/l

Agar (Biokar Diagnostics): . . . 20 g/l

Osmosed water: . . . qs 1000 ml pH corrected to 7 with NaOH

Sterilization 20 min at 120° C.

Preculture Medium

Sucrose: . . . 100 g/l

Sterilization by filtration on 0.22 μm

Yeast extract: . . . 9.7 g/l pH corrected to 7.0 (with NaOH)/sterilization 20 min at 120° C. 1 drop antifoam Inoculum: One 10 μl loop starting from the 3$^{rd}$ subculturing Subculture Medium Idem preculture medium Inoculum: 10% of preculture (15 ml)

Production Medium

1—Sucrose base

Sucrose . . . 200 g/l

Sterilization by filtration on 0.22 μm

Yeast extract: . . . 4.2 pH corrected to 7.0 (with NaOH)/sterilization 20 min at 120° C. 10 drops antifoam 2—Beet molasses base (at 84.1% DP2)

Beet molasses . . . 357 g

Sterilization by filtration on 0.22 μm

Yeast extract: . . . 4.2 g/l pH corrected to 7.0 (with NaOH)/sterilization 20 min at 120° C. 10 drops antifoam Inoculum: 6% subculture (90 ml)

Example 2

Optimization of the Sucrose Base Turanose Production Conditions with the I-4604 Strain Several agitation, aeration and pH conditions were tested separately during the production step. The preculture, subculture and production media were the same as in example 1. The optimizations were carried out in a 2l fermentor.

Effect of Agitation

The agitation was tested at 300, 500 and 700 rpm, the other parameters being 30° C., 1 vvm and a pH regulated at 6. The results were the following.

300 rpm

| | Time (h) | | | |
|---|---|---|---|---|
| | 0 | 15 | 22.5 | 39.5 |
| Sucrose (g/l) | 198.1 | 74.2 | 33.9 | 2.3 |
| Turanose (g/l) | 3 | 76 | 98.3 | 113.8 |
| Sucrose consum. (g/l/h) | — | 8.26 | 5.37 | 1.86 |
| Turanose prod. (g/l/h) | — | 4.87 | 2.97 | 0.91 |
| Turanose yield (%) | — | — | 58.04 | — |

500 rpm

| | Time (h) | | | |
|---|---|---|---|---|
| | 0 | 15 | 22.5 | 39.5 |
| Sucrose (g/l) | 193.2 | 68.5 | 32.1 | 4.7 |
| Turanose (g/l) | 2.8 | 70.8 | 90.7 | 103.1 |
| Sucrose consum. (g/l/h) | — | 8.31 | 4.85 | 1.61 |
| Turanose prod. (g/l/h) | — | 4.53 | 2.65 | 0.73 |
| Turanose yield (%) | — | — | 54.56 | — |

700 rpm

| | Time (h) | | | |
|---|---|---|---|---|
| | 0 | 15 | 22.5 | 39.5 |
| Sucrose (g/l) | 202.2 | 67.3 | 31.9 | 4.6 |
| Turanose (g/l) | 2.8 | 72.8 | 93.1 | 107.7 |
| Sucrose consum. (g/l/h) | — | 8.99 | 4.72 | 1.61 |
| Turanose prod. (g/l/h) | — | 4.67 | 2.71 | 0.86 |
| Turanose yield (%) | — | — | 53.02 | — |

Effect of Aeration

The aeration was tested at 0.5, 1 and 1.5 vvm, the other parameters being 30° C., 300 rpm and a pH regulated at 6. The results were the following.

0.5 vvm

| | Time (h) | | |
|---|---|---|---|
| | 0 | 14.25 | 22.75 |
| Sucrose (g/l) | 196.2 | 64.1 | 19.7 |
| Turanose (g/l) | 3.3 | 74.4 | 100 |
| Sucrose consum. (g/l/h) | — | 9.27 | 5.22 |

-continued

|  | Time (h) | | |
|---|---|---|---|
|  | 0 | 14.25 | 22.75 |
| Turanose prod. (g/l/h) | — | 4.99 | 3.01 |
| Turanose yield (%) | — | — | 54.79 |

1 vvm

|  | Time (h) | | |
|---|---|---|---|
|  | 0 | 14.25 | 22.75 |
| Sucrose (g/l) | 189.6 | 74.3 | 26.8 |
| Turanose (g/l) | 2.9 | 71.3 | 98.9 |
| Sucrose consum. (g/l/h) | — | 8.09 | 5.59 |
| Turanose prod. (g/l/h) | — | 4.80 | 3.25 |
| Turanose yield (%) | — | — | 58.97 |

1.5 vvm

|  | Time (h) | | |
|---|---|---|---|
|  | 0 | 14.25 | 22.75 |
| Sucrose (g/l) | 201.6 | 74.7 | 26.3 |
| Turanose (g/l) | 3.5 | 76.3 | 104.4 |
| Sucrose consum. (g/l/h) | — | 8.91 | 5.69 |
| Turanose prod. (g/l/h) | — | 5.11 | 3.31 |
| Turanose yield (%) | — | — | 57.56 |

Effect of pH

The pH was tested at 5.5, 6 and 6.5, the other parameters being 30° C., 300 rpm and 1 vvm. The results were the following.

pH Regulated at 5.5

|  | Time (h) | | |
|---|---|---|---|
|  | 0 | 15 | 23 |
| Sucrose (g/l) | 194.3 | 74.7 | 32.8 |
| Turanose (g/l) | 3.7 | 69.4 | 89.9 |
| Sucrose consum. (g/l/h) | — | 7.97 | 5.24 |
| Turanose prod. (g/l/h) | — | 4.38 | 2.56 |
| Turanose yield (%) | — | — | 53.37 | pH Regulated at 6

|  | Time (h) | | |
|---|---|---|---|
|  | 0 | 15 | 23 |
| Sucrose (g/l) | 198.1 | 62.2 | 24.3 |
| Turanose (g/l) | 3.4 | 82.5 | 105 |
| Sucrose consum. (g/l/h) | — | 9.06 | 4.74 |
| Turanose prod. (g/l/h) | — | 5.27 | 2.81 |
| Turanose yield (%) | — | — | 58.46 | pH Regulated at 6.5

|  | Time (h) | | |
|---|---|---|---|
|  | 0 | 15 | 23 |
| Sucrose (g/l) | 197.9 | 64.2 | 27.2 |
| Turanose (g/l) | 3.5 | 77.1 | 99.7 |
| Sucrose consum. (g/l/h) | — | 8.91 | 4.63 |
| Turanose prod. (g/l/h) | — | 4.91 | 2.83 |
| Turanose yield (%) | — | — | 56.36 |

The most appropriate conditions were defined as an agitation of 300 rpm, an aeration of 1 vvm and a pH regulated at 6.0.

In addition, the amount of sucrose used during the fermentation step and also the culture medium used were the subject of optimization.

Effect of the Starting Sucrose Concentration

Two starting concentrations were tested, namely 100 and 200 g/l of sucrose.

Preculturing was carried out at 30° C., 160 rpm, for 23 h 30 in a medium at a pH of 7, comprising 30 g/l of sucrose and 30 g/l of SOLULYS 048E sterilized separately for 20 min at 120° C. and 1 drop of antifoam. The production was carried out at 30° C., 300 rpm, 1 vvm for 25 h in a medium at a pH of 7, comprising 100 or 200 g/l of sucrose and 30 g/l of SOLULYS 048E sterilized separately for 20 min at 120° C. and 10 drops of antifoam. The pH is noted at 5.8 at 6 h of fermentation and regulated at 5.5 starting from 9 h.

100 g/l of Starting Sucrose

|  | Time (h) | | | |
|---|---|---|---|---|
|  | 0 | 6 | 9 | 25 |
| Sucrose (g/l) | 101.6 | 45.3 | 16.9 | <0.5 |
| Turanose (g/l) | 2.1 | 28.1 | 40.7 | 35.1 |

200 g/l of Starting Sucrose

| Time (h) | 0 | 6 | 9 | 25 |
|---|---|---|---|---|
| Sucrose (g/l) | 190.3 | 150.6 | 117.7 | 11 |
| Turanose (g/l) | 1.9 | 26.2 | 44.8 | 92.9 |

The starting sucrose concentration of 200 g/l gives better results.

Effect of Medium

Three Groups of Culture Media were Tested

|  | Preculture | Subculture | Production |
|---|---|---|---|
| Medium 1 | Sucrose 100 g/l<br>Yeast extract 14 g/l<br>SOLULYS 048E<br>5 g/l | Sucrose 100 g/l<br>Yeast extract 10 g/l<br>SOLULYS 048E<br>5 g/l | Sucrose 200 g/l<br>$NH_4H_2PO_4$ 1.3 g/l<br>$(NH_4)_2HPO_4$<br>1.3 g/l<br>$MgSO_4 \cdot 7H_2O$<br>0.4 g/l<br>$Fe(NH_4)_2(SO_4)_2$<br>0. g/l |
| Medium 2 | Sucrose 100 g/l<br>Yeast extract<br>9.7 g/l | Sucrose 100 g/l<br>Yeast extract<br>9.7 g/l | Sucrose 200 g/l<br>Yeast extract<br>4.2 g/l |
| Medium 3 | Sucrose 100 g/l<br>SOLULYS 048E<br>30 g/l | Sucrose 100 g/l<br>SOLULYS 048E<br>30 g/l | Sucrose 200 g/l<br>SOLULYS 048E<br>13 g/l |
| Conditions | 30° C., 165 rpm,<br>18 h | 30° C., 165 rpm,<br>9 h | 30° C., 300 rpm,<br>pH 6 |

The Results Obtained are the Following

|  | Time (h) | 0 | 15 | 20.5 | 24 | 39.5 |
|---|---|---|---|---|---|---|
| Medium 1 | sucrose | 204 | 75.8 | 45.3 | 28.8 | 1.1 |
| (g/l) | turanose | — | 70.6 | 88.5 | 102.6 | 111.8 |
| Medium 2 | sucrose | 204.8 | 66.8 | 37.7 | 22.7 | 1 |
| (g/l) | turanose | — | 78.8 | 96.9 | 104.8 | 114.5 |
| Medium 3 | sucrose | 193.8 | 94.2 | 58.9 | 44.7 | 7.8 |
| (g/l) | turanose | — | 65.8 | 79 | 90.9 | 113.2 |

Medium 2 appears to be the most appropriate since it enables time to be saved.

Example 3

Production of Turanose Using the I-4604 Strain

The production of turanose using the I-4604 strain in 20 l fermentors was carried out.

The fermentation was carried out starting from sucrose and from molasses. The Protocol was the following.

Preculturing

| Sucrose | 100 g/l |
|---|---|
| SOLULYS ® 048E | 15 g/l |
| Erol 18 | 1 drop |

The whole mixture is sterilized at 120° C. for 20 min and adjusted to pH 7.

The preculturing is carried out in three 500 ml Erlenmeyer flasks for 24 h at 30° C. and 120 rpm.

Subculturing

| Sucrose | 100 g/l |
|---|---|
| SOLULYS ® 048E | 30 g/l |
| Erol 18 | 0.5 ml/l |

The whole mixture is sterilized at 120° C. for 20 min and adjusted to pH 7.

The subculturing is carried out in a fermentor in a volume of 15 l for 19 h at 30° C., 300 rpm and 1 vvm.

Production

| Sucrose | 100 g/l | sterilized at 120° C. for 10 min |
|---|---|---|
| Erol 18 | 0.5 ml/l | idem |
| SOLULYS ® 048E | 30 g/l | sterilized at 120° C. for 20 min |

The pH is adjusted to pH 6. The culturing is carried out in a fermentor in a volume of 15 l at 30° C., 300 rpm and 1 vvm.

Results

| Time (h) (g/l) | 14 | 22 | 30 | 36 | 47 |
|---|---|---|---|---|---|
| Sucrose | 45.9 | 11.7 | 1.3 | 0 | 0 |
| Glucose | 0 | 0 | 0 | 0 | 0 |
| Fructose | 17.1 | 18.3 | 14.5 | 7.3 | 0 |
| Isomaltulose | 4.1 | 4.5 | 4.8 | 4.9 | 4.8 |
| Trehalulose | 9.5 | 10.7 | 11.1 | 11.8 | 11.1 |
| Turanose | 93.9 | 97.3 | 97.7 | 102.1 | 102.8 |
| Richness | 75.3 | 74.4 | 76.3 | 80.9 | 86.6 |
| Yield (%) | 60.9 | 51.7 | 49.1 | 51.05 | 51.4 |

The average results over 4 tests are the following:

Yield (turanose/sucrose): 53%

Duration: 45 to 50 h

Final sugar composition:
  Turanose: 106 g/l (i.e., 86% of the sugars)
  Trehalulose: 12 g/l
  Isomaltulose: 5 g/l Since the culture medium initially proposed was simple and inexpensive, the effects of the temperature, of the pH, of the oxygenation level and of the mode of sucrose provision were subsequently studied.

The table below recapitulates the results of all the tests carried out:

| conditions | Duration | Abs 620 nm | fructose | isomaltulose | trehaltulose | turanose | 2 keto acid | Richness/ DP2 (%) | Yield/ sucrose (%) |
|---|---|---|---|---|---|---|---|---|---|
| STANDARD | 47 h | 20 | 0 | 5 | 12 | 106 |  | 86.0 | 53.0 |
| suc 100 g/l | 15 h | 21.65 | 0 | 2.8 | 4.7 | 53.4 |  | 87.7 | 53.4 |
| suc FB 100 g/l | 15 h | 21.4 | 0.7 | 1.9 | 3.8 | 35.2 |  | 86.1 | 35.9 |
| 27° C.- 2 × 100 g/l | 56 h | 22.21 | 0 | 4.4 | 9.8 | 99.6 |  | 87.5 | 49.8 |
| 500 RPM | 40 h | 22.17 | 27.1 | 5.3 | 13.5 | 111.4 | 6.6 | 85.6 | 56.0 |
| 400 RPM | 36 h | 17.56 | 26.3 | 5.4 | 12.2 | 105.9 | 7.5 | 85.7 | 53.5 |
| 33° C. | 30 h | 16.78 | 21 | 5.4 | 12.4 | 97.2 |  | 84.5 | 48.6 |
| 38° C. | 41 h | 16.16 | 28.1 | 6.3 | 14.9 | 96.9 |  | 82.0 | 48.5 |
| 27° C. | 47 h | 18.97 | 0 | 4.6 | 10.5 | 105 |  | 87.4 | 52.5 |
| pH 5.0 | 21 h | 2.04 |  |  | no growth |  |  |  |  |
| pH 7.0 | 41 h | 15.6 | 25.4 | 4.5 | 12.8 | 92.8 |  | 84.3 | 46.4 |

No modification had a significantly positive effect, but the following conclusions can however be drawn:
- the pH should be maintained at 6.0;
- the temperature should be maintained below 30° C. The optimum even appears to be close to 27° C.;
- an excessively high oxygenation level (agitation of 400 or 500 rpm) slows down the consumption of sucrose and leads to a strong production of 2-ketogluconic acid;
- the addition of a second preculturing step does not provide any advantage;
- it is of no advantage to introduce the sucrose gradually (FB=fed-batch).

Example 4

Purification of Turanose from the I-4604 Strain Fermentation Must

1—Fermentation Must Purification Steps

The separation of the biomass was carried out by centrifugation at 12,000 g. The supernatant was still cloudy. In order to remove this cloudiness, a treatment with powdered black carbon (1% of SX+) and a filtration on a Cofram EKS plate filter were carried out. The filtrate obtained was clearer, but not decolored.

Demineralization was carried out on strong cation (C150) and weak anion (4228). The load of the product before demineralization was 170 meq/l. The resistivity of the purified product was less than 5 kOhm since it contained several organic acids. The organic acid composition is indicated in the tables below.

In order to improve the richness before crystallization, an ultrafiltration was carried out on 1 kD. This step made it possible to retain the coloration and the products having molecular weights greater than 1 kD.

2—Crystallization

The crystallization was carried out at ambient temperature, after having brought to boiling a mixture of 100 g of product at 70 bx and 200 ml of 96% ethanol. The separation of the crystals and of the mother liquors was carried out on a Büchner funnel given the low viscosity of the mixture. Under these conditions, for 2 liters of fermentor used, 70 g of crystals (richness in turanose 98-99%) were recovered, i.e., a weight yield of 30%.

The crystals exhibited a good degree of richness, as illustrated by the tables below.

| Results in g/l | |
|---|---|
| Turanose | 115.6 |
| Trehalulose | 14 |
| Isomaltulose | 6.3 |
| Glucosylated glyceric acid | ~5 |
| Fructose | 2.8 |
| 2-Ketoglutaric acid | ~2 |
| Citric acid | ~2 |
| Succinic acid | ~1 |
| Glucosylated lactic acid | ~3 |

| Results in %/crude | |
|---|---|
| Dry matter | 99.8 |
| Fructose | <0.05 |
| Glucose | <0.05 |
| Glucosylated lactic acid | <0.05 |
| Palatinose | 1.1 |
| Trehalulose | 0.2 |
| Other DP2 | 0.3 |

These various purification steps made it possible to obtain turanose having a good degree of richness.

The invention claimed is:

1. A biologically pure *Serratia plymuthica* strain deposited on Mar. 7, 2012, with the CNCM (National Collection of Microorganism Cultures) under accession number 1-4604.

2. The strain as claimed in claim 1, characterized in that said strain produces turanose with a weight yield of at least 20%, 30%, 40% or 50% by weight turanose per sucrose.

3. The strain as claimed in claim 1, wherein said strain produces turanose with a weight yield of at least 30% by weight of turanose per sucrose.

4. The strain as claimed in claim 1, wherein said strain produces turanose with a weight yield of at least 40% by weight of turanose per sucrose.

5. The strain as claimed in claim 1, wherein said strain produces turanose with a weight yield of at least 50% by weight of turanose per sucrose.

6. A biologically pure *Serratia plymuthica* mutant strain that produces turanose, said mutant strain being obtained from the strain of claim 1 by culturing, mutagenesis or genetic modification, and said mutant strain produces turanose with a weight yield of at least 20% by weight turanose per sucrose.

7. The mutant strain as claimed in claim 6, characterized in that said mutant strain produces turanose with a weight yield of at least 30%, 40% or 50% by weight turanose per sucrose.

8. The mutant strain as claimed in claim 6, wherein said mutant strain produces turanose with a weight yield of at least 30% by weight of turanose per sucrose.

9. The mutant strain as claimed in claim 6, wherein said mutant strain produces turanose with a weight yield of at least 40% by weight of turanose per sucrose.

10. The mutant strain as claimed in claim 6, wherein said mutant strain produces turanose with a weight yield of at least 50% by weight of turanose per sucrose.

11. A method for producing turanose, comprising culturing the strain as claimed in claim 1 in production medium comprising sucrose and recovering the turanose, and optionally purifying the turanose.

12. The method as claimed in claim 11, characterized in that the strain is cultured at a pH of between 5.5 and 7, an aeration of from 0.5 to 1.5 vvm, under agitation conditions of between 250 and 700 rpm, and at a temperature of from 25 to 38° C.

13. The method as claimed in claim 11, characterized in that the strain is cultured at a pH maintained at 6, a temperature of from 27 to 30° C., under agitation conditions of between 250 and 350 rpm, and an aeration of 1 vvm.

14. The method as claimed in claim 11, in which the starting sucrose concentration in the production medium is between 100 and 300 g/l.

15. The method as claimed in claim 11, in which the production medium further comprises 2 to 6 g/l of yeast extract.

16. The method as claimed in claim 11, comprising the purification of turanose, said purification comprising a fermentation must centrifugation step, steps of treatment with powdered black carbon and of filtration of the supernatant, a demineralization step, a step of ultrafiltration with a cut-off threshold of 1 kD, and then a filtrate crystallization step.

17. The method as claimed in claim 11, in which the production medium further comprises 4 g/l of yeast extract.

18. The method as claimed in claim 11, in which the production medium further comprises 10 to 30 g/l of corn steep liquor.

19. A method for producing turanose, comprising culturing the mutant strain as claimed in claim 6 in a production medium comprising sucrose and recovering the turanose, and optionally purifying the turanose.

\* \* \* \* \*